(12) United States Patent
Kawai et al.

(10) Patent No.: US 7,235,241 B2
(45) Date of Patent: Jun. 26, 2007

(54) MONOMER PROTEIN WITH BONE MORPHOGENETIC ACTIVITY AND MEDICINAL AGENT CONTAINING THE SAME FOR PREVENTING AND TREATING DISEASES OF CARTILAGE AND BONE

(75) Inventors: Shinji Kawai, Paris (FR); Michio Kimura, Kanagawa (JP); Yoshifumi Muraki, Tokyo (JP); Mieko Katsuura, Tokyo (JP)

(73) Assignee: Biopharm Gesellschaft zur biotechnologischen Entwicklung von Pharmaka mbH, Heidelberg (DE)

( * ) Notice: Subject to any disclaimer, the term of this patent is extended or adjusted under 35 U.S.C. 154(b) by 190 days.

(21) Appl. No.: 10/751,451

(22) Filed: Jan. 6, 2004

(65) Prior Publication Data
US 2006/0019886 A1    Jan. 26, 2006

Related U.S. Application Data

(62) Division of application No. 09/701,121, filed as application No. PCT/IB99/00866 on May 14, 1999, now abandoned.

(51) Int. Cl.
*A61K 38/18* (2006.01)
*C07K 14/475* (2006.01)
*C12N 1/20* (2006.01)
*C12P 21/06* (2006.01)
*C07H 21/04* (2006.01)

(52) U.S. Cl. ............... 424/185.1; 435/69.1; 435/252.3; 435/252.33; 435/254; 435/320.1; 530/350; 536/23.5

(58) Field of Classification Search .................... None
See application file for complete search history.

(56) References Cited

U.S. PATENT DOCUMENTS 5,158,934 A    10/1992  Ammann et al.

5,658,882 A  *  8/1997  Celeste et al. ................ 514/12

FOREIGN PATENT DOCUMENTS

| EP | 0 866 125 A | 9/1998 |
|---|---|---|
| WO | WO 92 14481 A | 9/1992 |
| WO | WO 92 19262 A | 11/1992 |
| WO | WO 97 04095 A | 2/1997 |

OTHER PUBLICATIONS

Ngo et al., 1994, The Protein Folding Problem and Tertiary Structure Prediction, pp. 491-495.*
Brunner et al, J Biol Chem 264(23): 13660-13664, 1989.*
Mason AJ, "Functional-analysis of the cysteine residues of Activin-A", Molecular Endocrinology, Mar. 1994, vol. 8, No. 3, pp. 325-332.
Amatayakul-Chantler et al., "Ser77!Transforming growth factor-beta1", J. Biol. Chem., vol. 269, No. 44, Nov. 4, 1994, pp. 27687-27691.
Hüsken-Hindi et al., "Monomeric activin A retrains high receptor binding affinity but exhibits low biological activity", J. Biol. Chem., vol. 269, No. 30, Jul. 29, 1994, pp. 19380-19384.
McDonald et al., "A structural superfamily of growth factors containing a cystine know motif", CELL, vol. 73, May 7, 1993, pp. 421-424.

* cited by examiner

*Primary Examiner*—Christina Chan
*Assistant Examiner*—Phuong Huynh
(74) *Attorney, Agent, or Firm*—Rothwell, Figg, Ernst & Manbeck

(57) ABSTRACT

This invention provides for a protein of the TGF-β superfamily in which the cysteine involved in the normal formation of homodimers is changed to another amino acid. These mutant proteins, as monomers, display higher bone morphogenetic activity than the wild-type protein dimers. Also provided is a method for producing and isolating these monomers by plasmid driven expression in various host systems including *E. coli*. In addition, the invention discloses the use of an agent containing purified monomers in preventing and treating diseases and problems affecting bone and/or cartilage.

4 Claims, 2 Drawing Sheets

SEQUENCE LISTING

<160> NUMBER OF SEQ ID NOS: 4

<210> SEQ ID NO 1
<211> LENGTH: 357
<212> TYPE: DNA
<213> ORGANISM: HUMAN
<220> FEATURE:

```
<221> NAME/KEY: CDS
<222> LOCATION: (1)..(357)
<223> OTHER INFORMATION: Relevant amino acid residues in SEQ ID NO 1
      from 1 to 82 and from 84 to 119 in WO 95/04819.
      Note : aminoacid residue 83 is alanine instead of cysteine.
<300> PUBLICATION INFORMATION:
<301> AUTHORS: HOTTEN, Gertrud
      NEIDHARDT, Helge
      PAULISTA, Michael
<302> TITLE: New growth/differentiation factor of the tgf-beta
      familie.
<310> PATENT DOCUMENT NUMBER: WO 95/04819
<311> PATENT FILING DATE: 1995-02-16

<400> SEQUENCE: 1 cca cta gca act cgt cag ggc aag cga ccc agc aag aac ctt aag gct    48
Pro Leu Ala Thr Arg Gln Gly Lys Arg Pro Ser Lys Asn Leu Lys Ala
 1               5                  10                  15 cgc tgc agt cgg aag gca ctg cat gtc aac ttc aag gac atg ggc tgg   96
Arg Cys Ser Arg Lys Ala Leu His Val Asn Phe Lys Asp Met Gly Trp
            20                  25                  30 gac gac tgg atc atc gca ccc ctt gag tac gag gct ttc cac tgc gag  144
Asp Asp Trp Ile Ile Ala Pro Leu Glu Tyr Glu Ala Phe His Cys Glu
        35                  40                  45 ggg ctg tgc gag ttc cca ttg cgc tcc cac ctg gag ccc acg aat cat  192
Gly Leu Cys Glu Phe Pro Leu Arg Ser His Leu Glu Pro Thr Asn His
 50                  55                  60 gca gtc atc cag acc ctg atg aac tcc atg gac ccc gag tcc aca cca  240
Ala Val Ile Gln Thr Leu Met Asn Ser Met Asp Pro Glu Ser Thr Pro
 65                  70                  75                  80 ccc acc gcc tgt gtg ccc acg cga ctg agt ccc atc agc atc ctc ttc  288
Pro Thr Ala Cys Val Pro Thr Arg Leu Ser Pro Ile Ser Ile Leu Phe
                85                  90                  95 att gac tct gcc aac aac gtg gtg tat aag cag tat gag gac atg gtc  336
Ile Asp Ser Ala Asn Asn Val Val Tyr Lys Gln Tyr Glu Asp Met Val
            100                 105                 110 gtg gag tcg tgt ggc tgt agg                                       357
Val Glu Ser Cys Gly Cys Arg
        115

<210> SEQ ID NO 2
<211> LENGTH: 119
<212> TYPE: PRT
<213> ORGANISM: HUMAN

<400> SEQUENCE: 2

Pro Leu Ala Thr Arg Gln Gly Lys Arg Pro Ser Lys Asn Leu Lys Ala
 1               5                  10                  15

Arg Cys Ser Arg Lys Ala Leu His Val Asn Phe Lys Asp Met Gly Trp
            20                  25                  30

Asp Asp Trp Ile Ile Ala Pro Leu Glu Tyr Glu Ala Phe His Cys Glu
        35                  40                  45

Gly Leu Cys Glu Phe Pro Leu Arg Ser His Leu Glu Pro Thr Asn His
 50                  55                  60

Ala Val Ile Gln Thr Leu Met Asn Ser Met Asp Pro Glu Ser Thr Pro
 65                  70                  75                  80

Pro Thr Ala Cys Val Pro Thr Arg Leu Ser Pro Ile Ser Ile Leu Phe
                85                  90                  95

Ile Asp Ser Ala Asn Asn Val Val Tyr Lys Gln Tyr Glu Asp Met Val
            100                 105                 110

Val Glu Ser Cys Gly Cys Arg
        115
```

```
<210> SEQ ID NO 3
<211> LENGTH: 39
<212> TYPE: DNA
<213> ORGANISM: HUMAN
<220> FEATURE:
<221> NAME/KEY: misc_feature
<222> LOCATION: (1)..(39)
<223> OTHER INFORMATION: Sense PCR primer for mutation introducing.

<400> SEQUENCE: 3
catgccatgg accccgagtc cacaccaccc accgcctgt                               39

<210> SEQ ID NO 4
<211> LENGTH: 37
<212> TYPE: DNA
<213> ORGANISM: HUMAN
<220> FEATURE:
<221> NAME/KEY: misc_feature
<222> LOCATION: Complement((1)..(37))
<223> OTHER INFORMATION: Reverse PCR primer for mutation introducing.

<400> SEQUENCE: 4
cccaagcttg catgcctgcc ggtcgactac ctacagc                                 37
```

MONOMER PROTEIN WITH BONE MORPHOGENETIC ACTIVITY AND MEDICINAL AGENT CONTAINING THE SAME FOR PREVENTING AND TREATING DISEASES OF CARTILAGE AND BONE

CROSS REFERENCE TO RELATED APPLICATION

This application is a divisional of U.S. Ser. No. 09/701,121 filed Jan. 3, 2001, now abandoned, which is a § 371 National Phase Entry Application from PCT/IB99/00866, filed May 14, 1999, and designating the U.S., which claims priority from Japanese Application No. 10/141,379 filed May 22, 1998.

BACKGROUND OF THE INVENTION (1) Field of the Invention

The present invention relates to a monomer protein having an amino acid sequence belonging to TGF-β superfamily, of which cysteine related to a dimer formation of a protein has been replaced with another amino acid. Moreover, the present invention relates to a method for preparing said monomer protein in a large amount and with a high purity by using Escherichia coli transformed with a plasmid containing a DNA sequence that can express said monomer protein. Furthermore, the present invention relates to an agent containing said monomer protein for preventing and treating a disease affecting bone and/or cartilage.

(2) Description of the Related Art

Currently, there are known estrogen, calcitonin, vitamin D3, its derivatives and derivatives of bisphosphonic acid as preventive or therapeutic agents for bone diseases. Recently, it has been reported that a bone morphogenetic activity is found in a series of a bone morphogenetic protein (hereinafter referred to as "BMP") belonging to TGF-β superfamily, from BMP-2 to BMP-14.

Moreover, it has been reported that a protein named GDF-5 or human MP52 has a bone morphogenetic activity (WO93/16099, WO95/04819, WO94/15949 and Nature Vol. 368, 1994, p. 639–643). It is considered that mature human MP52 is a protein having 120 amino acid residues starting with alanine at an N-terminal, and its amino acid sequence has been described in these patent applications.

These proteins exist as a homodimer having a single disulfide bond in nature. On the contrary, the manufacture of their recombinant protein is carried out using their homodimers or heterodimers to yield a protein showing the activity. For example, human MP52 has been reported in the publication of unexamined application, JP 031098/97. Meanwhile, there are two types named type I receptor and type II receptor in the receptors of TGF-β superfamily. Intercellular signal transmission via receptors of TGF-β superfamily containing these bone morphogenetic proteins (dimers) requires simultaneous combination of these proteins to both type I and type II receptors, and it is considered that a polymer is formed by gathering of two or more dimers to do intercellular signal transmission (Bone, Vol. 19, 1996, p. 569–574). It has been considered that for polymer formation it is important that the protein should be a dimer. The activity in a monomer has not yet been found. Moreover, preparation for these monomer recombinants has not yet been carried out.

SUMMARY OF THE INVENTION

The present inventors have attempted a mass production of human MP52 monomers by a genetic engineering technology using Escherichia coli. Namely, the present inventors constructed a plasmid of DNA sequence encoding the amino acid sequence having 119 residues described in SEQ ID NO: 1 of the Sequence Listing, among which the codon of the cysteine residue of No. 83, that is related to a disulfide bond between MP52 monomer molecules, was converted to the codon of alanine. In addition, the inventors have succeeded in expressing a large amount of human MP52 monomers using Escherichia coli by using the plasmid and refolding to produce monomers of the protein described in SEQ ID NO: 1 of the Sequence Listing with a high purity and a very high yield.

It has been surprisingly found that the monomer has the activity to induce differentiation to osteocytes in some cell lines (MC3T3-E1 and ATDC5) despite that in conventional understanding, only a dimer has a bone morphogenetic activity. The present invention has been completed by observing that the activity to induce differentiation is two-fold higher than that of the dimer on the basis of weight concentration.

DESCRIPTION OF THE PREFERRED EMBODIMENT

Figure 1:
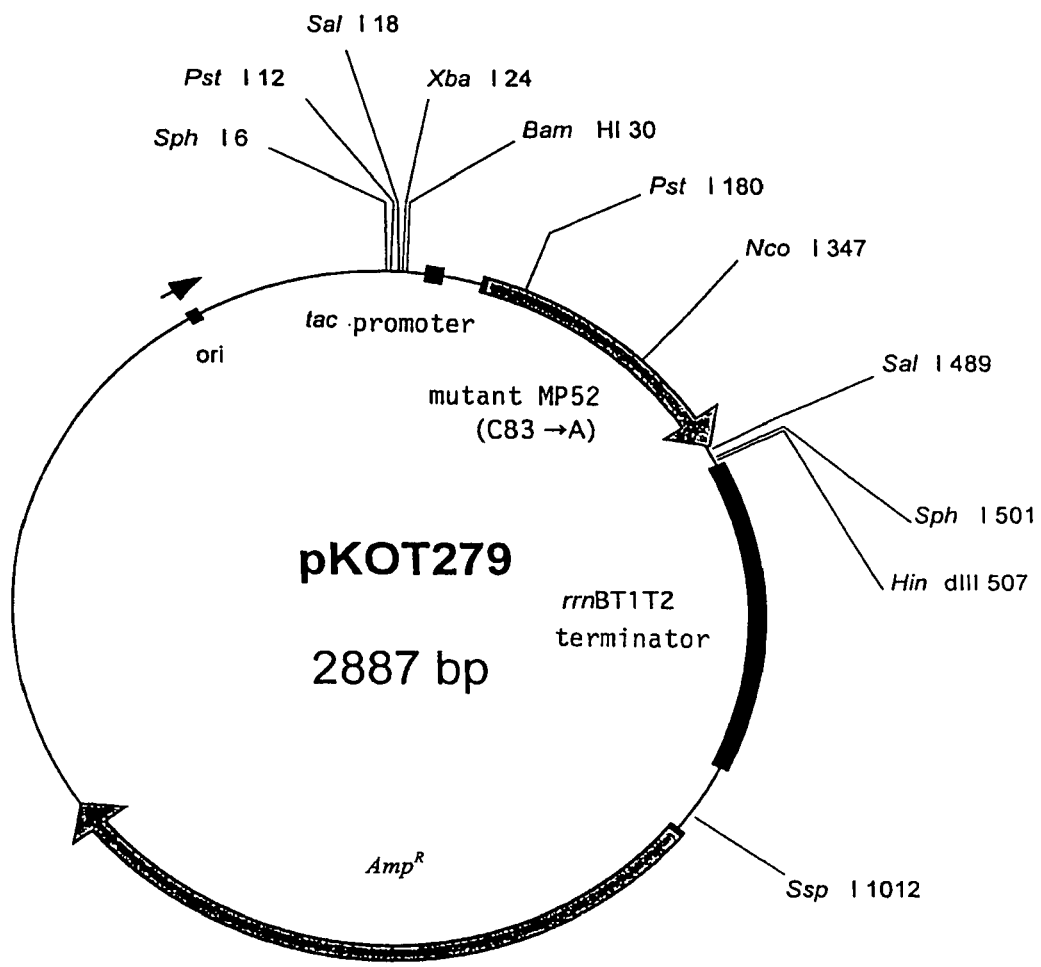
FIG. 1 is a plasmid map of the expression vector (pKOT279) obtained in Example 1 (2).

Namely, the present invention relates to a monomer protein having an amino acid sequence belonging to TGF-β superfamily, of which cysteine related to a dimer formation of the protein has been replaced with another amino acid, a method for expressing said monomer protein, and an agent for preventing and treating a disease affecting bone and/or cartilage containing one or more than one said monomer proteins.

The present invention relates to a monomer protein having an amino acid sequence belonging to TGF-β superfamily, of which cysteine related to a dimer formation of the protein has been replaced with another amino acid. The TGF-β superfamily of the present invention means BMP-2, BMP-4, BMP-5, BMP-6, BMP-7, BMP-12, BMP-13, BMP-14, human MP52, GDF-5, GDF-6, GDF-7, etc. Another amino acid may be any amino acid selected from a group consisting of alanine, threonine, serine and valine in consideration of the size of an amino acid side chain. The most preferable amino acid is alanine.

The present invention relates to a monomer protein having an amino acid sequence described in SEQ ID NO.: 1 of the Sequence Listing. In detail, the monomer protein is a protein in which cysteine is replaced with alanine, and the aforesaid cysteine contributes to intermolecular disulfide bond of a human MP52 dimer having an intermolecular disulfide bond, and is present at the $83^{rd}$ position of the amino acid sequence of SEQ ID NO.: 1 of the Sequence Listing. The monomer protein obtained by the present invention shows a two-fold higher activity in inducing differentiation than a dimer protein made from the monomer protein.

Furthermore, the present invention relates to a method for preparation of said monomer protein to express by using *Escherichia coli*, yeast, insect cells, and mammal cells that have been transformed by a plasmid having a DNA sequence capable of expression of said monomer protein. In detail, the present invention relates to a method for preparation of a protein having 119 amino acid residues derived from human MP52 represented by SEQ ID NO.: 2 of the Sequence Listing, by employing *Escherichia coli*. In other words, the present invention relates to construction of a plasmid having a DNA sequence that encodes an amino acid sequence in which methionine is added to the N-terminal of the amino acid sequence derived from human MP52 in which alanine has replaced cysteine of the $83^{rd}$ position from 119 residues represented by SEQ ID NO.: 1 of the Sequence Listing. For human MP52 cDNA, a mature portion was solely amplified by polymerase chain reaction (PCR method) by using a plasmid vector as a template DNA containing cDNA described in WO93/16099. The PCR method used in the invention means general amplification from a very small amount of a fragment of DNA or RNA of a nucleic acid by the method described in U.S. Pat. No. 4,683,195.

In the present invention, a mutant monomer protein was obtained by construction of a plasmid having a DNA sequence that encodes an amino acid sequence in which methionine is added to the N-terminal of the amino acid sequence represented by SEQ ID NO.: 1 of the Sequence Listing, by transformation of the plasmid to *Escherichia coli*, by solubilization of the inclusion body obtained by culturing the *Escherichia coli* and by purification. The present invention relates to a method for preparation of the protein by refolding to have an activity and purifying said protein to a monomer protein described in SEQ ID NO.: 2 of the Sequence Listing. Concretely, for the monomer protein of the present invention, MP52 mutant monomer protein was obtained by applying the solubilized inclusion bodies of *Escherichia coli* to a SP-Sepharose FF column (Amersham Pharmacia Biotech) and to Superdex 200 pg column (Amersham Pharmacia Biotech). Subsequently, the purified monomer protein of the present invention is obtained by refolding and then by passing through a reversed phase HPLC RESOURCE RPC column (Amersham Pharmacia Biotech). The physical and chemical properties of the present monomer protein obtained are analyzed on the basis of data of an N-terminal amino acid sequence, an amino acid composition, and electrophoresis.

The biological properties of the monomer protein of the present invention were evaluated by the activity to induce differentiation of two kinds of osteoblast cell lines of which promoting alkaline phosphatase activity was already found in a human MP52 dimer. In comparison in the weight concentration, the monomer protein of the present invention showed a two-fold higher activity than that of the conventional dimer protein.

The present invention relates to a preventive or therapeutic agent for cartilage and/or bone diseases having amino acid sequence represented by SEQ ID NO.: 2 of the Sequence Listing as an effective ingredient. In detail, the monomer protein of the present invention has an activity to induce differentiation, i.e., an morphogenetic activity for cartilage and bone, and therefore, relates to a preventive or therapeutic agent for osteoporosis, congenital bone and/or cartilage diseases, and osteoarthritis such as joint osteoarthritis and hip joint osteoarthritis, or arthrosteitis, damage of cartilage such as damage of meniscus, regeneration of bone and cartilage deficit caused by injury and tumor dissection, bone and cartilage deficit, fracture, congenital cartilage and/or bone diseases such as achondroplasia, dyschondrogenesis, achondrogenesis, palatoschisis, and dysosteogenesis, and a deficit of root of teeth and a tooth socket.

Furthermore, the protein of the present invention, having bone and cartilage morphogenetic activity, can be used for therapy of bone graft in an aesthetic surgery field. The therapy includes a field of veterinary surgery.

As in systemic administration method, intravenous, intramuscular, and intra-abdominal administrations are possible; in an intravenous administration, an intravenous drip can be applied in addition to a general intravenous injection.

An injection preparation can be, for example, a powder preparation for injection. In the case, one or more kinds of appropriate water-soluble excipient such as mannitol, sucrose, lactose, maltose, glucose, or fructose are added to dissolve in water, divided into vials or ampoules, freeze-dried, and hermetically sealed to make as a product.

For a local administration method, there is a method to cover the surface of a cartilage, bone, or tooth of the site with the present protein by using collagen paste, fibrin glue, or other adhesives. Among them, a bone used for bone graft can be also applied to an artificial bone conventionally used as well as a natural bone. The artificial bones include bones made of natural materials or artificial inorganic materials such as metals, ceramics, and glasses. The artificial inorganic materials are preferably exemplified by hydroxyapatite. For example, a metal is used for an internal material and hydroxyapatite for an external material of an artificial bone. Furthermore, the present protein can be administered to a carcinomatous tissue to enhance reconstruction of a bone. It is also possible to use for cartilage grafting.

An administrative dose is determined by a physician in charge in consideration of the following various factors affecting the action of the present protein: the weight of bone and cartilage to reconstruct, the site and condition of the damage of bone and cartilage, sex and age of a patient, severity of the infection, administration duration, and other clinical factors. The dose can vary according to the kind of a carrier used for reconstruction that is realized in combination with the present protein. In general, concerning the dose, ca. $10–10^6$ ng as the present monomer protein for a given wet weight of a bone and cartilage in the use as a composition containing a carrier and $0.1–10^4$ µg for one patient as an injection for local and in systemic application are preferably administered in the frequency ranging from once a day to once a week.

A multiplier effect can be expected by simultaneous application of a known growth factor such as insulin-like growth factor-I for regeneration of a bone and cartilage.

Thus, a monomer made by substitution of cysteine of a protein belonging to TGF-β superfamily and industrial manufacture for a monomer have not been reported. The monomer has a morphogenetic activity for cartilage and bone and is useful as a therapeutic agent for cartilage and/or bone diseases. Furthermore, the monomer protein of the present invention shows a two-fold higher activity per weight than that of a dimer of the protein and allows a half reduction of an effective dose of a therapeutic agent for cartilage and/or bone diseases. This fact can be applied to manufacture of before-mentioned bone morphogenetic factors belonging to TGF-β superfamily.

The monomer protein derived from human MP52 and having an amino acid sequence described in SEQ ID NO.: 2 of the Sequence Listing has a two-fold higher activity in a osteoblast cell line to induce differentiation than that of the dimer and useful as a preventive or therapeutic agent for cartilage and/or bone diseases. Furthermore, a change of an amino acid of the monomer protein of the present invention reduces cysteine and thus, it makes easy preparation of a mass and pure monomer protein possible by using *Escherichia coli*.

EXAMPLES

This invention shall be more illustratively explained by way of the following Examples. The following Examples are to be considered in all respects as illustrative and not restrictive.

Example 1

Preparation of a Human MP52 Monomer Expression Vector (1) Isolation of a Mature Region of a Human MP52 Mutant The human MP52 monomer was prepared by replacing cysteine residue which is regarded as forming a dimer with another amino acid residue in order to prevent the formation of a dimer with the human MP52 monomer. In the present invention, the codon of cysteine (TGC) of the $83^{rd}$ of the mature human MP52 starting with proline described in SEQ ID NO.: 1 of the Sequence Listing of WO 96/33215 was converted to the codon of alanine (GCC).

The substitution of an amino acid residue was carried out by using a PCR primer (forward direction) in which an objective mutation has been introduced with reference to the mutation method (Section 8.5) by polymerase chain reaction (PCR) described in Current Protocols in Molecular Biology (John Wiley & Sons, Inc.). The sequence of the PCR primer used was described in SEQ ID NO.: 3 as a sense primer and in SEQ ID NO.: 4 as a reverse primer.

PCR was performed by using a human MP52 expression vector (pKOT245) described in WO96/33215 as a template DNA (10 ng), each 10 pM sense primers and reverse primers, DNTP of 0.4 mM, $MgCl_2$ of 2.5 mM, and LA Taq DNA polymerase (5U, Takara Shuzo Co., Ltd; catalog No. RR013A) in the same test tube. The 30 cycles of reaction was operated of which one cycle included denaturation (94° C., 1 min), primer annealing (55° C., 1 min), and primer elongation (72° C., 2 min). The PCR product was digested by restriction enzymes NcoI and HindIII, separated by electrophoresis with 1.5% low melting point agarose (FMC BioProducts Co., catalog No. 5170B) and purified to obtain a DNA fragment having a ca. 170 bases as an objective product.

The human monomer MP52 expression vector (pKOT279) was prepared by replacing a DNA fragment of NcoI-HindIII in which mutation was introduced by aforementioned method with NcoI-HindIII region of a human monomer MP52 expression vector (pKOT277) made by modifying a human monomer MP52 expression vector (pKOT245) described in WO96/33215. Concretely, by preparing the human monomer MP52 expression vector (pKOT277) from which lacZ promoter, that is transcribed in the reverse direction to a MP52 existing in the downstream of the terminator of the human monomer MP52 expression vector (pKOT245) described in WO96/33215, by digesting said MP52 expression vector (pKOT277) by restriction enzymes NcoI and HindIII, separating by electrophoresis in 1.5% low melting point agarose (FMC BioProducts Co., cat. No. 5170B) and by purifying, a DNA fragment having 2717 base pairs was obtained for an objective product. The DNA fragment and the DNA fragment of ca. 170 base pairs to which mutation was introduced, were ligated by using DNA Ligation Kit (Takara Shuzo Co., Ltd., catalog No. 6021) to prepare a human monomer MP52 expression vector (pKOT279, 2.9 kb). The vector was deposited in National Institute of Bioscience and Human-Technology, Agency of Industrial Science and Technology, Ministry of International Trade and Industry, 1-3, Higashi 1-chome, Tsukuba-shi Ibaraki-ken 305-8566 Japan, in Feb. 5, 1998 (Deposit no. Bikoukenki no. FERM P-16625) and transferred to the International Depository Authority under Budapest Treaty on Feb. 3, 1999 (Deposit No. FERM BP-6637). For the base sequence of the human MP52 monomer expression vector of the present invention, introduction of the objective mutation and correctness of the base sequence (other sequence than that of the site to which a mutation was introduced) of the human MP52 produced were confirmed by using a DNA sequencer (Amersham Pharmacia Biotech, ALF).

(2) Transformation

Transformation was experimented according to rubidium chloride method of Kushner et al. (Genetic Engineering p. 17, Elsevier. 1978). Namely, pKOT279 was introduced to *Escherichia coli* W3110M according to above method to make the *Escherichia coli* to express a protein in the present invention.

Example 2

Cultivation (1) Cultivation

The *Escherichia coli* to express a protein of the present invention was precultured in a modified SOC culture medium (Bacto tryptone 20 g/L, Bacto yeast extract 5 g/L, NaCl 0.5 g/L, $MgCl_2$ 0.95 g/L, and glucose 3.6 g/L), 100 mL of cell suspension (Bacto tryptone 20 g/L, citric acid 4.3 g/L, $K_2HPO_4$ 4.675 g/L, $KH_2PO_4$ 1.275 g/L, NaCl 0.865 g/L, $FeSO_4.7H_2O$ 100 mg/L, $CuSO_4.5H_2O$ 1 mg/L, $MnSO_4.nH_2O$ 0.5 mg/L, $CaCl_2.2H_2O$ 2 mg/L, $Na_2B_4O_7.10H_2O$ 0.225 mg/L, $(NH_4)_6Mo_7O_{24}$ 0.1 mg/L, $ZnSO_4.7H_2O$ 2.25 mg/L, $CoCl_2.6H_2O$ 6 mg/L, $MgSO_4.7H_2O$ 2.2 g/L, thiamine HCl 5.0 mg/L, methionine 2 g/L, and glucose 3 g/L) was added to 5 L of a culture medium for production to culture in a 10 L culture vessel with aerated stirring, isopropyl-β-D-thiogalactopyranoside of 1 mM concentration in a stage reached a logarithmic multiplication prophase ($OD_{550}$=50) was added to culture by $OD_{550}$ beyond 150. In the culture, the temperature was regulated to 31° C. and the pH was regulated to 7.2 by adding ammonia. Dissolved oxygen concentration was regulated to 50% of air saturation by increasing stirring speed in order to prevent decrease in dissolved oxygen concentration. A 50% glucose solution containing 0.1 M phosphate was added to make glucose concentration 0.2% with reference to rapid rise of dissolved oxygen concentration as an indication in order to make a higher cell concentration in culture.

(2) Preparation of the Inclusion Bodies from *Escherichia coli*

The culture solution obtained by said method was passed three times through a high pressure homogenizer (LAB40-10RBF1, APV, Gohrin Co.) under 560 bar pressure to break cells and centrifuge to collect a precipitate containing the inclusion bodies.

Example 3

Purification (1) Solubilization of the Inclusion Bodies from *Escherichia coli*

The inclusion bodies collected were washed twice with 20 mM Tris-HCl buffer solution (pH 8.3) containing 1 M urea and 5 mM EDTA and centrifuged at 4° C. and 3,000×g for 30 min; the precipitate obtained was solubilized by sonication in 20 mM Tris-HCl buffer solution (pH 8.3) containing 8 M urea, 50 mM NaCl, 64 mM DTT, and 5 mM EDTA.

(2) Purification of Denatured Monomer Protein

The solubilized solution was centrifuged at 4° C. and 20,000×g for 30 min and the supernatant was collected. The supernatant collected was applied to SP-Sepharose FF (Amersham Pharmacia Biotech) column equilibrated with 20 mM Tris-HCl buffer solution (pH 8.3), 6 M urea, 10 mM DTT, and 1 mM EDTA, washed with the solution, and eluted with the solution containing 0.4 M NaCl. The eluate was subjected to gel filtration with a Superdex 200 pg column (Amersham Pharmacia Biotech) equilibrated by 20 mM Tris-HCl buffer solution (pH 8.3), 6 M urea, 0.5 M NaCl, 10 mM DTT, and 1 mM EDTA to obtain a single denatured monomer protein.

(3) Refolding 50 mM Na-Glycine buffer solution (pH 9.8), 0.5 M NaCl, 20 mM CHAPS, and 3 mM GSSG (oxidized glutathione) of nine times quantity were added to the solution of the denatured monomer protein obtained by above treatment followed by stirring to refold at 4° C. for 20 h.

(4) Purification of a Monomer Protein Having an Activity.

The sample refolded was diluted 2.8 times with 14 mM $NaH_2PO_4$ and subjected to isoelectric precipitation. The precipitate was collected by centrifugation at 3,000×g for 20 min and dissolved in 0.05% TFA. The solution was applied to a RESOURSE RPC column (Amersham Pharmacia Biotech) of reverse-phase HPLC previously equilibrated with 0.05% TFA and eluted with 0.05% TFA and 0–50% acetonitrile gradient. The eluate was monitored by an absorptiometer at 280 nm absorbancy to obtain a fraction of purified monomer protein of the present invention. To the protein fraction, 5 N NaOH was added to make in the range of between pH 6.5 and 7.5 for precipitation in isoelectric point. The precipitate was collected by centrifugation of 10,000×g for 10 h and dissolved in 10 mM HCl to make ca. 3 mg/mL to obtain a monomer protein having an activity of the present invention.

(i) N-terminal sequence analysis

The N-terminal analysis of the amino acid composition of the purified monomer protein of the present invention obtained above was carried out by using a sequencer (Applied Biosystem, Model 476A).

(ii) Amino acid composition analysis

The amino acid composition of the purified monomer protein of the present invention obtained above was examined by an amino acid analyzer (Waters, PICO. TAG. WORK STATION).

(iii) Electrophoretic analysis

The molecular weight of the purified monomer protein of the present invention obtained above was investigated by SDS-PAGE under a non-reduced condition to be a molecular weight of ca. 1.4 kDa.

As the results given by (i), (ii), and (iii), it has been found that the monomer protein of the present invention is a monomer protein having 119 amino acid residues of which N-terminal starts with Pro shown in SEQ ID NO.: 2 of the Sequence Listing.

Example 4

Measurement of Biological Activity

Figure 2:
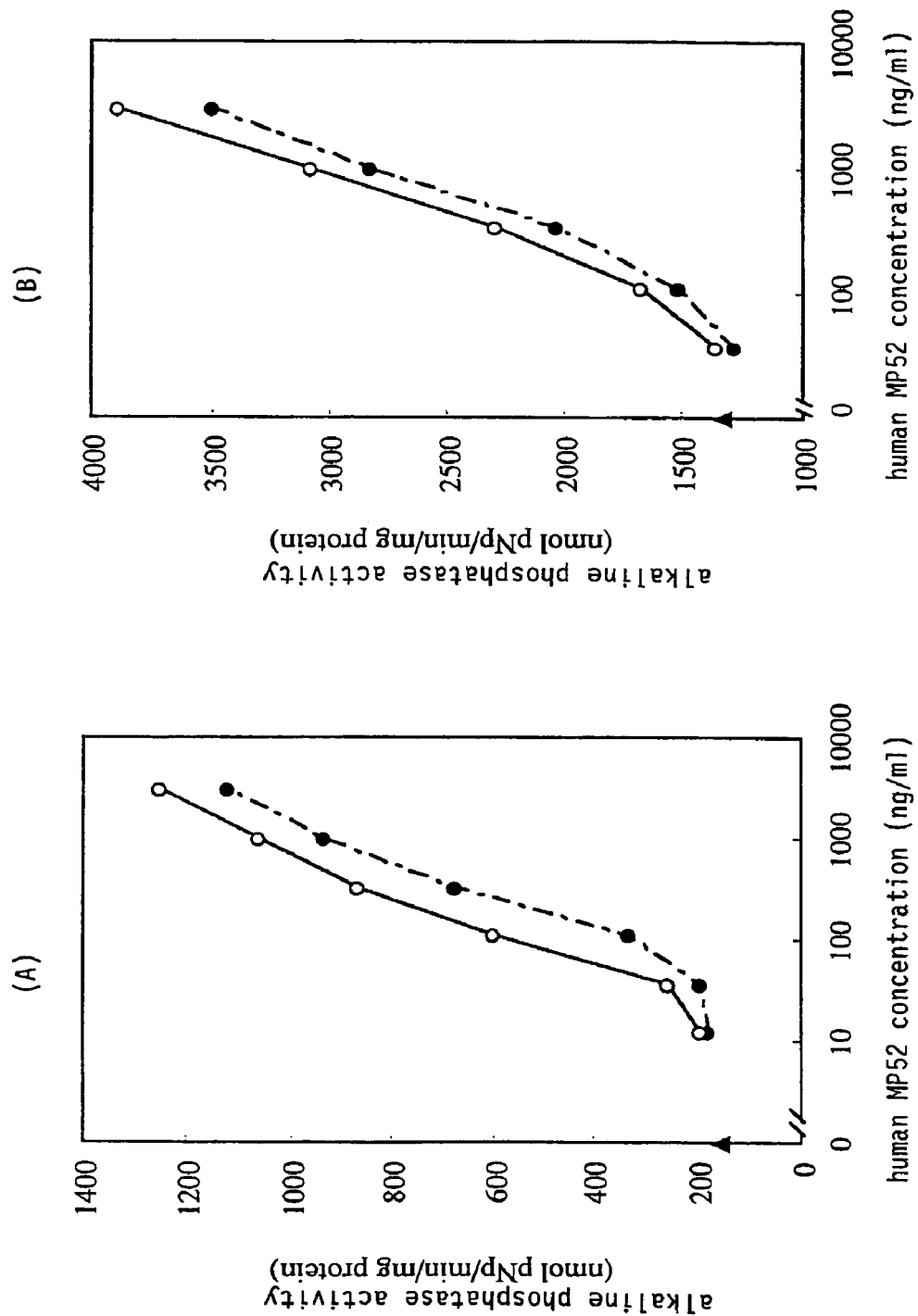
FIG. 2 is a comparative figure of osteoblast differentiation promoting activities between the monomer of the present invention and human MP52 dimer. (A) shows the activity in MC3T3-E1 cells and (B) shows that in ATDC5 cells. The white circle shows the activity of the monomer and the black circle shows that of human MP52 dimer.

A differentiation inducing activity was evaluated by employing two cultured cell lines; ATDC5 (Riken Gene Bank, RCB 0565) to differentiate like a cartilage cell derived from a mouse embryonic cell and MC3T3-E1 (Riken Gene Bank, RCB 1126) having properties like those of an osteoblast derived from a mouse, on the basis of reference to alkaline phosphatase promoting activity of said protein. The result is shown in FIG. 2.

ATDC5 and MC3T3-E1 of the concentration of 10,000 cells per 1 mL were suspended in DF culture medium (Gibco Ltd.) containing 5% bovine fetus serum and in MEM-α⁻ medium (Gibco Ltd.) containing 10% bovine fetus serum, respectively, and inoculated in 24 plates at 1 mL per 1 well to culture at 37° C. for 3 days under 5% $CO_2$.

Subsequently, the cells were rinsed with the MEM-α⁻ medium without serum, a natural dimer or a monomer protein diluted gradationally with the MEM-α⁻ medium containing 0.3% bovine albumin was added 0.5 mL per 1 well to start induction of differentiation. The cultivation was carried out for 3 days, the cells were rinsed with PBS (20 mM phosphate buffer solution, 150 mM NaCl, pH 7.4) twice and 250 μL of cytolytic solution (0.2% NP-40, 1 mM $MgCl_2$) was added and kept standing at 37° C. for 2 hours. Following this step, the total volume of the cytolytic solution containing cells broken was transferred to a micro tube and centrifuged (10,000×g, 5 min) to use its supernatant for assay.

An enzyme activity was measured by observing the rise of absorbancy of p-nitrophenol (pNp) being the dissociated product derived from p-nitrophenyl phosphate as the substrate of the final concentration of 10 mM by dissolving in 0.1 M glycine buffer, pH 10.4, 1 mM $ZnCl_2$, and 1 mM $MgCl_2$, at 405 nm.

The rise of absorbancy was observed every 2 min for 40 min and the alkaline phosphatase promoting activity (μM pNp/min) was calculated on the basis of the data of the range showing linearity.

In addition, the protein concentration of the same supernatant was known by using a BCA Protein Assay Kit (Amersham Pharmacia Biotech) and the alkaline phosphatase activity per protein was represented by nmol pNp/min/mg protein.

What is claimed is:

1. A monomer human MP52 protein comprising an amino acid sequence belonging to the TGF-β super family, wherein said monomer protein comprises the amino acid sequence described in SEQ ID NO:2 or the amino acid sequence described in SEQ ID NO:2 wherein alanine at position 83 is replaced with a serine, threonine or valine and wherein said monomer protein induces differentiation of osteoblasts measured by promoting alkaline phosphatase activity.

2. A preparation comprising the monomer protein according to claim 1 in combination with an excipient.

3. The preparation according to claim 2, wherein said monomer protein induces differentiation of osteoblasts.

4. A method for producing the monomer human MP52 protein of claim 1 wherein the method comprises transforming a host cell selected from the group consisting of *Escherichia coli,* a yeast cell, an insect cell and a mammalian cell with a plasmid comprising a DNA sequence that encodes the monomer protein of claim 1 and purifying said protein.

* * * * *